(12) United States Patent
Hou et al.

(10) Patent No.: US 10,315,034 B2
(45) Date of Patent: Jun. 11, 2019

(54) SYSTEMS AND METHODS FOR REDUCING PAIN DURING SPINAL CORD STIMULATION TRIAL

(71) Applicant: PACESETTER, INC., Sylmar, CA (US)

(72) Inventors: Wenbo Hou, Santa Clara, CA (US); Alexander Kent, Mountain View, CA (US); Edward Karst, Los Angeles, CA (US); Gene A. Bornzin, Simi Valley, CA (US); Riddhi Shah, San Jose, CA (US); Caroline Jordan, Los Altos Hills, CA (US); Yelena Nabutovsky, Mountain View, CA (US)

(73) Assignee: PACESETTER, INC., Sylmar, CA (US)

( * ) Notice: Subject to any disclaimer, the term of this patent is extended or adjusted under 35 U.S.C. 154(b) by 409 days.

(21) Appl. No.: 15/041,233

(22) Filed: Feb. 11, 2016

(65) Prior Publication Data
US 2017/0216597 A1    Aug. 3, 2017

Related U.S. Application Data

(60) Provisional application No. 62/290,308, filed on Feb. 2, 2016.

(51) Int. Cl.
*A61N 1/00* (2006.01)
*A61N 1/36* (2006.01)
*A61N 1/32* (2006.01)
*A61N 1/05* (2006.01)

(52) U.S. Cl.
CPC ....... *A61N 1/36071* (2013.01); *A61N 1/0551* (2013.01); *A61N 1/0558* (2013.01); *A61N 1/325* (2013.01); *A61N 1/36062* (2017.08)

(58) Field of Classification Search
USPC .......................................... 607/116
See application file for complete search history.

(56) References Cited

U.S. PATENT DOCUMENTS

2013/0338730 A1* 12/2013 Shiroff ................ A61N 1/0558
607/48

* cited by examiner

*Primary Examiner* — Nicole F Lavert
*Assistant Examiner* — Nicole F Johnson

(57) ABSTRACT

The present disclosure provides a spinal cord stimulation (SCS) system. The system includes at least one SCS lead including a lead body, at least one distal electrode located at a distal end of the lead body, the at least one distal electrode configured to apply electrical stimulation to a stimulation target of a patient, and a pain reduction assembly coupled to the lead body and configured to reduce post-operation pain at an incision site associated with implantation of the at least one SCS lead. The system further includes a pulse generator coupled to the at least one SCS lead and configured to control electrical stimulation delivered to the patient via the at least one SCS lead.

14 Claims, 8 Drawing Sheets

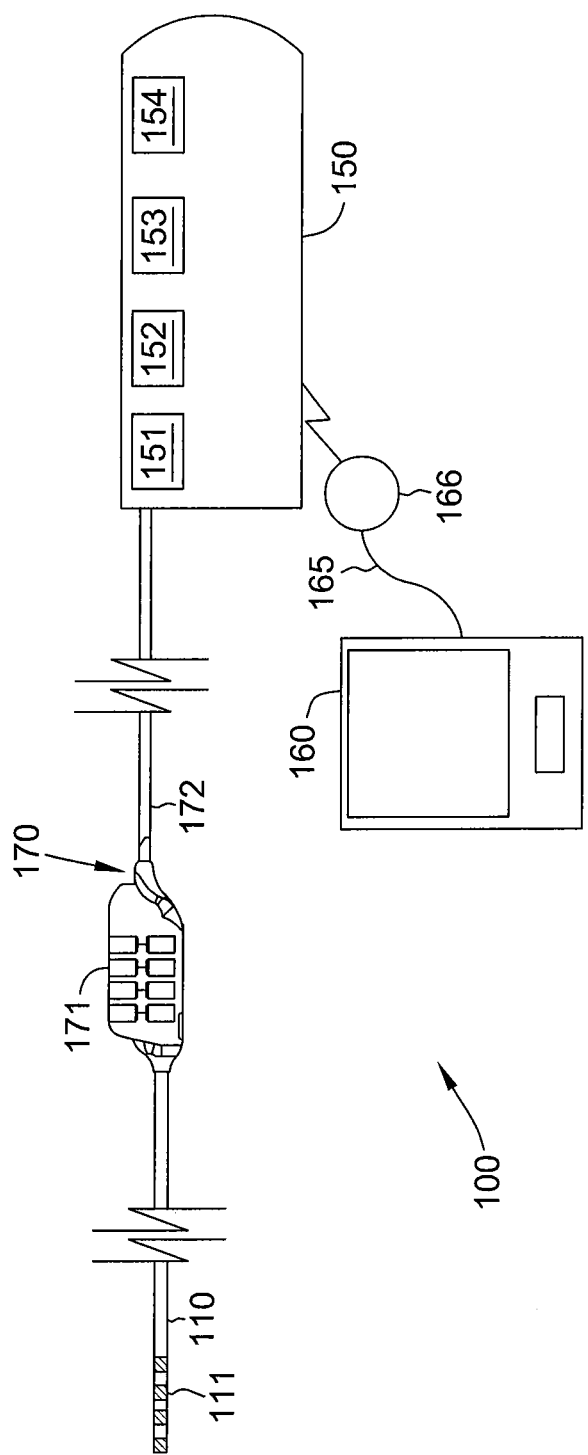

SYSTEMS AND METHODS FOR REDUCING PAIN DURING SPINAL CORD STIMULATION TRIAL

CROSS REFERENCE TO RELATED APPLICATIONS

This application claims the benefit of U.S. Provisional Application Ser. No. 62/290,308, filed Feb. 2, 2016.

A. FIELD OF THE DISCLOSURE

The present disclosure relates generally to neurostimulation systems, and more particularly to spinal cord stimulation trials.

B. BACKGROUND ART

Neurostimulation is a treatment method utilized for managing the disabilities associated with pain, movement disorders such as Parkinson's Disease (PD), dystonia, and essential tremor, and also a number of psychological disorders such as depression, mood, anxiety, addiction, and obsessive compulsive disorders.

Neurostimulation systems include spinal cord stimulation (SCS) systems. Before having a permanent SCS system implanted, patients may undergo an SCS trial to determine whether SCS will be successful in reducing pain. However, it is believed that only roughly 20% of chronic pain patients who are indicated for SCS undergo a trial. This may be the result of lack of familiarity with SCS therapy by the treating physician and/or patient apprehension about the invasiveness of the trial.

For example, SCS lead implantation may include using an epidural needle, such as a 14-gauge Tuohy needle, to puncture the patient's skin and back musculature to gain access to the epidural space. After the puncturing, the needle lead is implanted into the epidural space. This damages tissue, which may cause inflammation and pain for several days.

In addition, a sizeable fraction of patients who undergo an SCS trial do not successfully convert to a permanent SCS system. Reasons for failure include lack of pain relief, lack of paresthesia, and discomfort resulting from stimulation. Further, post-operative pain from the trial may mask SCS-generated improvements in reducing pain. Accordingly, there is a need for an SCS trial system that increases accessibility of SCS therapy and that improves the trial-to-permanent success rate.

BRIEF SUMMARY OF THE DISCLOSURE

In one embodiment, the present disclosure is directed to a spinal cord stimulation (SCS) system. The system includes at least one SCS lead including a lead body, at least one distal electrode located at a distal end of the lead body, the at least one distal electrode configured to apply electrical stimulation to a stimulation target of a patient, and a pain reduction assembly coupled to the lead body and configured to reduce post-operation pain at an incision site associated with implantation of the at least one SCS lead. The system further includes a pulse generator coupled to the at least one SCS lead and configured to control electrical stimulation delivered to the patient via the at least one SCS lead.

In another embodiment, the present disclosure is directed to a spinal cord stimulation (SCS) lead. The SCS lead includes a lead body, at least one distal electrode located at a distal end of the lead body, the at least one distal electrode configured to apply electrical stimulation to a stimulation target of a patient, and at least one peripheral nerve field stimulation electrode configured to deliver electrical stimulation to tissue proximate to an incision site to reduce post-operation pain at the incision site associated with implantation of the SCS lead.

In another embodiment, the present disclosure is directed to a spinal cord stimulation (SCS) lead. The SCS lead includes a lead body, at least one distal electrode located at a distal end of the lead body, the at least one distal electrode configured to apply electrical stimulation to a stimulation target of a patient, and a slidable sheath coupled to the lead body, the sheath configured to deliver at least one compound to tissue proximate to an incision site to reduce post-operation pain at the incision site associated with implantation of the SCS lead.

In some embodiments, the SCS lead in the systems and methods described may include a drug delivery system that facilitates delivering one or more drugs to tissue of the patient.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 1 is a schematic view of one embodiment of a stimulation system.

DETAILED DESCRIPTION OF THE DISCLOSURE

Figure 2A:
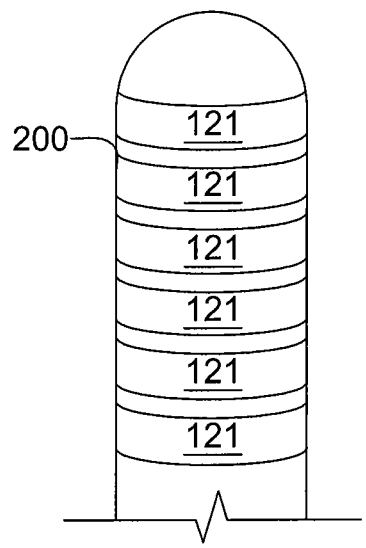
FIGS. 2A-2C are schematic views of stimulation portions that may be used with the stimulation system of FIG. 1.

The present disclosure provides systems and methods that facilitate reducing post-operation pain at an incision site for an SCS trial by using local peripheral nerve stimulation and/or drug release methods. In some embodiments, the spinal cord and/or dorsal root ganglia may be stimulated to target dermatomes that correspond to an incision site. Proximal electrodes on an SCS needle lead may also be used to apply peripheral nerve stimulation (PNS) to reduce post-operation pain. Further, a mesh embedded with one or more pain-relieving drugs may be attached to a lead body to reduce post-operation pain.

Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue of the spinal cord for the purpose of chronic pain control. While a precise understanding of the interaction between the applied electrical energy and the nervous tissue is not fully appreciated, it is known that application of an electrical field to spinal nervous tissue can effectively inhibit certain types of pain transmitted from regions of the body associated with the stimulated nerve tissue to the brain. Some types of electrical stimulation applied near the spinal cord may be able to replace the sensation of chronic pain with "paresthesia" (a subjective sensation of numbness or tingling) in the afflicted bodily regions. Other types of electrical stimulation may be able to inhibit the sensation of pain with little or no paresthesia.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. Stimulation may also be applied to the dorsal root ganglia (DRG) and/or peripheral nerves to reduce pain. The stimulation leads are then tunneled to another location within the patient's body to be electrically connected with a pulse generator or, alternatively, to an "extension."

Referring now to the drawings and in particular to FIG. 1, a stimulation system is indicated generally at 100. Stimulation system 100 generates electrical pulses for application to tissue of a patient, or subject, according to one embodiment. Stimulation system 100 includes an implantable pulse generator (IPG) 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of implantable pulse generator 150 for execution by the microcontroller or processor to control the various components of the device.

Implantable pulse generator 150 may comprise one or more attached extension components 170 or be connected to one or more separate extension components 170. Alternatively, one or more stimulation leads 110 may be connected directly to implantable pulse generator 150. Within implantable pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from implantable pulse generator 150 and conducted through the conductors of lead body 172 are provided to stimulation lead 110. The pulses are then conducted through the conductors of stimulation lead 110 and applied to tissue of a patient via electrodes 111. Any suitable known or later developed design may be employed for connector portion 171.

Stimulation lead(s) 110 may include a lead body of insulative material about a plurality of conductors within the material that extend from a proximal end of stimulation lead 110 to its distal end. The conductors electrically couple a plurality of electrodes 111 to a plurality of terminals (not shown) of stimulation lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 2B:
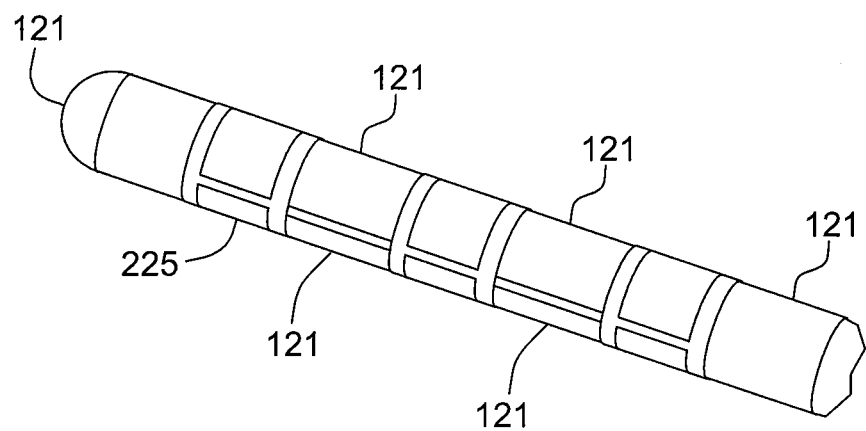
Figure 2C:
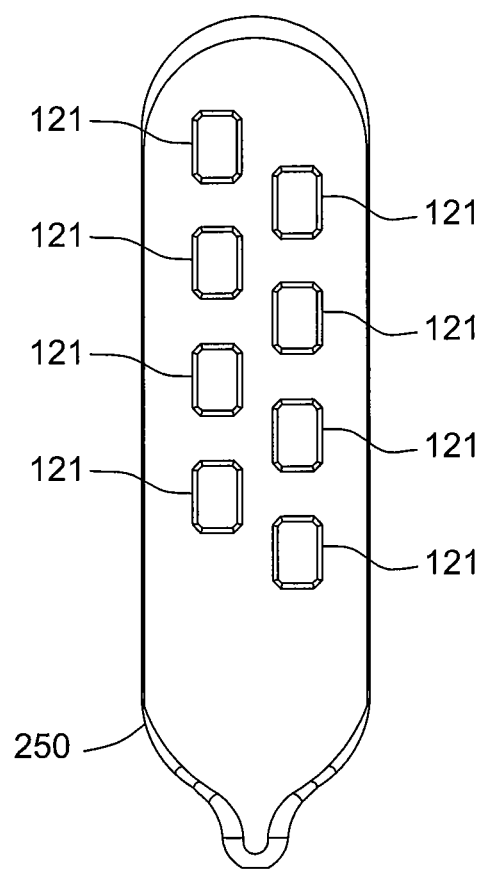

FIGS. 2A-2C respectively depict stimulation portions 200, 225, and 250 for inclusion at the distal end of stimulation lead 110. Stimulation portions 200, 225, and 250 each include a plurality of electrodes 121. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Stimulation portion 250 includes multiple planar electrodes on a paddle structure.

A controller device 160 may be implemented to recharge battery 153 of implantable pulse generator 150 (although a separate recharging device could alternatively be employed). A "wand" 165 may be electrically connected to controller device through suitable electrical connectors (not shown). The electrical connectors are electrically connected to a coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The systems and methods described herein facilitate reducing post-operation pain at an incision site for an SCS trial by using local peripheral nerve stimulation and/or drug release methods. In some embodiments, the spinal cord and/or dorsal root ganglia may be stimulated to target dermatomes that correspond to the incision site. Proximal electrodes on an SCS needle lead may also be used to apply peripheral nerve stimulation (PNS) to reduce post-operation pain, as described herein. Distal electrodes on the SCS needle lead are implanted inside the epidural space and are used for neuropathic pain treatment. The proximal electrodes are one example of a pain reduction assembly.

In other embodiments, the pain reduction assembly may be a mesh embedded with one or more pain-relieving drugs and may be attached to a lead body to reduce post-operation pain. The drugs may be delivered using a controlled release technique. Alternatively, the drugs may be delivered using an external pump, an osmotic pump, and/or using iontophoresis.

After implantation, the systems and methods described herein are used to apply electrical stimulation to the dorsal column, dorsal root(s), dorsal root ganglia (DRG), or peripheral nerve(s) to determine the effectiveness of SCS or peripheral nerve stimulation (PNS) in treating the patient's pain. The applied electrical stimulation may be burst stimulation, tonic stimulation, high-frequency stimulation, etc. If this testing is successful (e.g., if the testing results in a reduction in pain of 50% or more), then SCS is likely to benefit the patient and the patient could proceed to a permanent SCS system.

As noted above, in one embodiment, dermatomes that correspond to an incision site may be targeted to reduce post-operative pain. Specifically, stimulation may be applied to a DRG target or spinal cord target that corresponds to the incision site. This stimulation may be accomplished using electrodes on the SCS lead used to treat chronic pain (as opposed to post-operative pain), or using electrodes on a lead that is separate from the SCS lead used to treat chronic pain.

Figure 3:
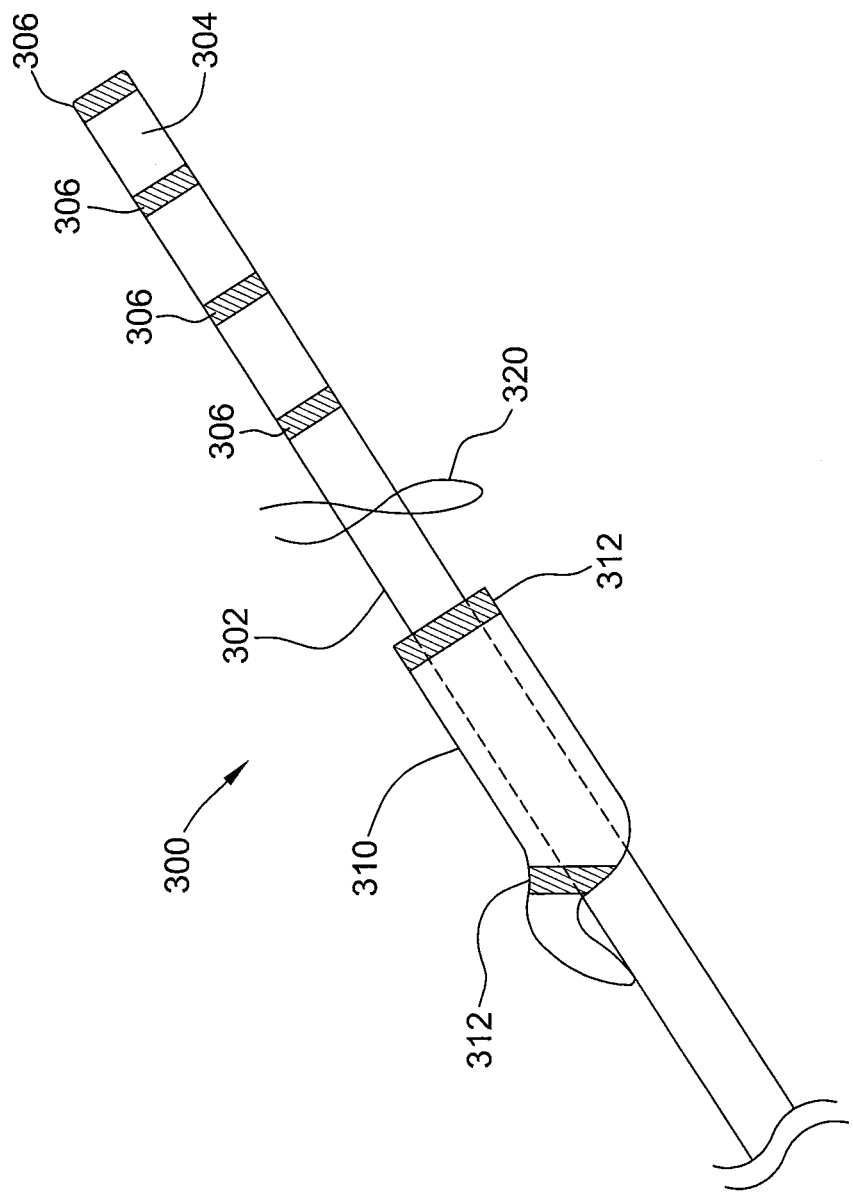
FIG. 3 is a schematic diagram of one embodiment of a spinal cord stimulation (SCS) lead that may be used to reduce post-operation pain.

FIG. 3 is a schematic diagram of another embodiment of an SCS lead 300 that may be used to reduce post-operation pain. SCS lead 300 includes a lead body 302 that includes a distal end 304. In this embodiment, distal end 304 includes a plurality of distal electrodes 306. After implantation, distal electrodes 306 are configured to apply electrical stimulation to the dorsal column, dorsal root(s), and/or dorsal root ganglia (DRG).

As shown in FIG. 3, in this embodiment, SCS lead 300 includes a slidable sheath 310 that is attached to lead body 302 and substantially surrounds lead body 302. Accordingly, sheath 310 is able to translate relative to lead body 302. Sheath 310 includes at least one peripheral nerve field stimulation (PNfS) electrode 312. PNfS modulates the transmission of pain signals to the brain near an associated electrode site. Thus, PNfS electrodes 312 are effectives in reducing post-operative pain in the vicinity of an incision. In this embodiment, sheath 310 includes two PNfS electrodes 312. Alternatively, sheath 310 may include any suitable number of PNfS electrodes 312. Sliding sheath 310 along lead body 301 facilitates adjusting a position of PNfS electrodes 312.

A suture 320 is used to anchor, or secure, SCS lead 300 to tissue during implantation. Specifically, after inserting SCS lead 300 into the patient, sheath 310 may be slid until PNfS electrodes 312 are located at an appropriate position (e.g., proximate to the incision site). Once sheath 310 is adjusted to a desired location, sheath 310 may be secured to surrounding tissue using suture 320. Alternatively, a separate suture may be used to secure sheath 310. Subsequently, PNfS electrodes 312 may be used to deliver stimulation to tissue injured during implantation, reducing post-operation pain or inducing paresthesia in the area near the incision site.

Figure 4:
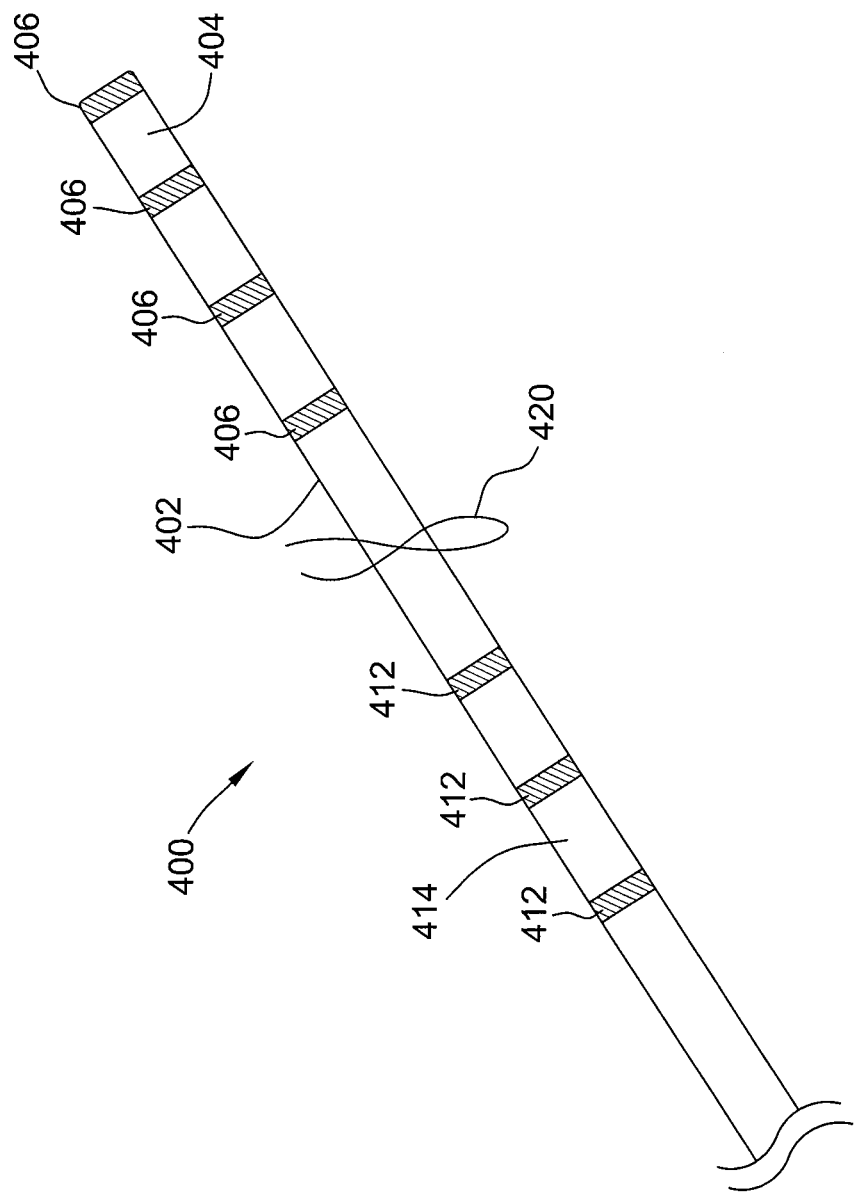
FIG. 4 is a schematic diagram of another embodiment of an SCS lead that may be used to reduce post-operation pain.

FIG. 4 is a schematic diagram of another embodiment of an SCS lead 400 that may be used to reduce post-operation pain. SCS lead 400 includes a lead body 402 that includes a distal end 404. In this embodiment, distal end 404 includes a plurality of distal electrodes 406. After implantation, distal electrodes 406 are configured to apply electrical stimulation to the dorsal column, dorsal root(s), and/or dorsal root ganglia (DRG).

As shown in FIG. 4, in this embodiment, SCS lead 400 also includes a plurality of PNfS electrodes 412 at a proximal portion 414 of lead body 402. In this embodiment, proximal portion 414 includes three PNfS electrodes 412. Alternatively, proximal portion 414 may include any suitable number of PNfS electrodes 412. The distance between distal electrodes 406 and PNfS electrodes 412 may be, for example, approximately 8 to 12 centimeters (cm). Notably, unlike PNfS electrodes 312 (shown in FIG. 3), the position of PNfS electrodes 412 along lead body 402 is not adjustable. Accordingly, the distance between distal electrodes 406 and PNfS electrodes 412 is selected to facilitate locating PNfS electrodes 412 proximate the incision site when distal electrodes 406 are proximate a stimulation target.

Similar to SCS lead 300 (shown in FIG. 3), SCS lead 400 includes a suture 420 used to anchor, or secure, SCS lead 400 to tissue during implantation. After implantation, PNfS electrodes 412 may be used to deliver stimulation to tissue injured during implantation, reducing post-operation pain. Suture 420 may be located proximate to PNfS electrodes 412 to facilitate securing them proximate the incision site. Alternatively, suture 420 may be located at any suitable position along lead body 402.

Figure 5:
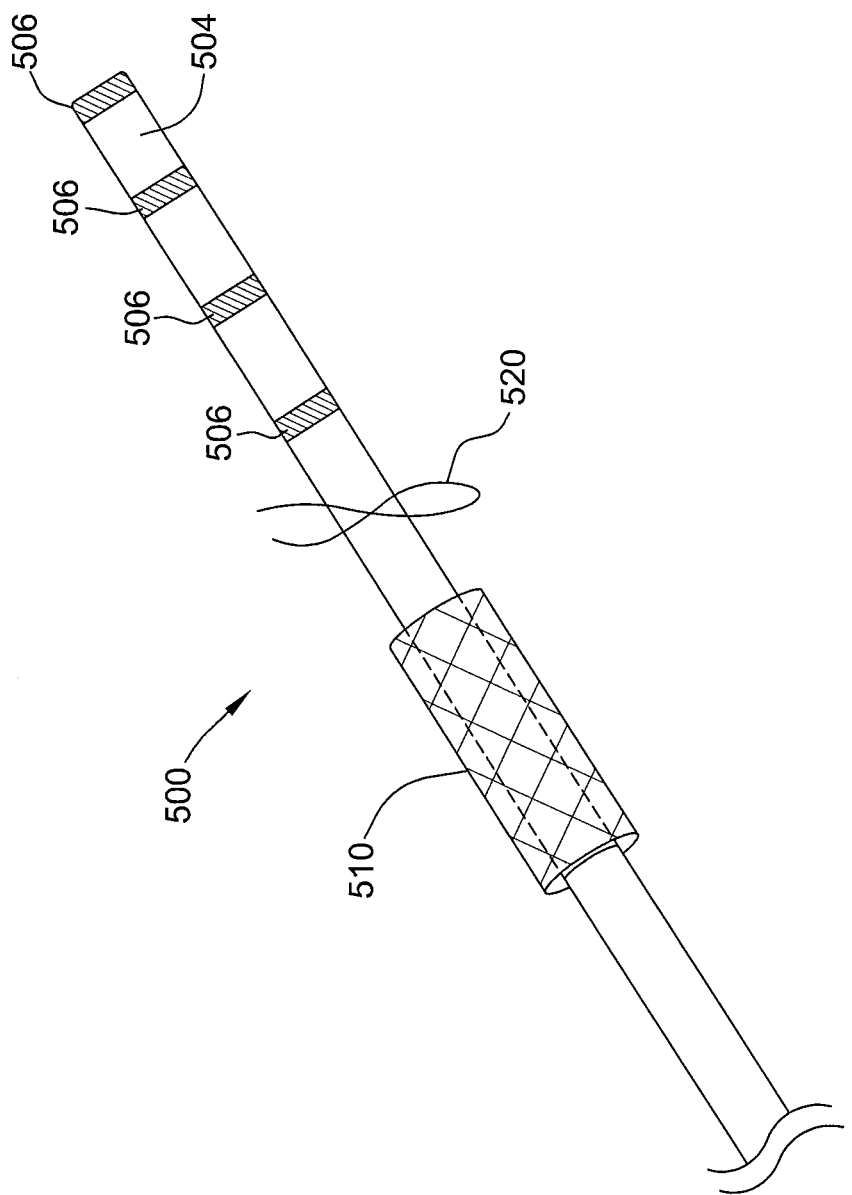
FIG. 5 is a schematic diagram of another embodiment of an SCS lead that may be used to reduce post-operation pain.

FIG. 5 is a schematic diagram of another embodiment of an SCS lead 500 that may be used to reduce post-operation pain. SCS lead 500 includes a lead body 502 that includes a distal end 504. In this embodiment, distal end 504 includes a plurality of distal electrodes 506. After implantation, distal electrodes 506 are configured to apply electrical stimulation to the dorsal column, dorsal root(s), and/or dorsal root ganglia (DRG).

As shown in FIG. 5, in this embodiment, SCS lead 500 includes a slidable sleeve 510 that is attached to lead body 502 and substantially surrounds lead body 502. Accordingly, sleeve 510 is able to translate relative to lead body 502. Sleeve 510 is a polyester mesh embedded with one or more pain relieving drugs. The pain relieving drugs may include, for example, lidocaine, pyrocarpine, carbanamide, etc. These drugs function as a local anesthetic and may be a mixture of anesthetic and antibiotic. In addition, anti-inflammatory medications (e.g., NSAIDs) may also be delivered using sleeve 510. In some embodiments, sleeve 510 includes a polyacrylamide layer or Dacron mesh that enables controlled release of the pain relieving drugs and/or other medications. Further, in some embodiments, sleeve 510 may include a biodegradable mesh impregnated with at least one compound, wherein the biodegradable mesh degrades over a period of time to effect a gradual release of the at least one compound.

A suture 520 is used to anchor, or secure, SCS lead 500 to tissue during implantation. Specifically, after inserting SCS lead 500 into the patient, sleeve 510 may be slid until it is located at an appropriate position (e.g., proximate the incision site). Once sleeve 510 is adjusted to a desired location, sleeve 510 may be secured to surrounding tissue using suture 320, or using a separate suture. Subsequently, sleeve 510 may be used to deliver pain relieving drugs to tissue injured during implantation, reducing post-operation pain.

Figure 6:
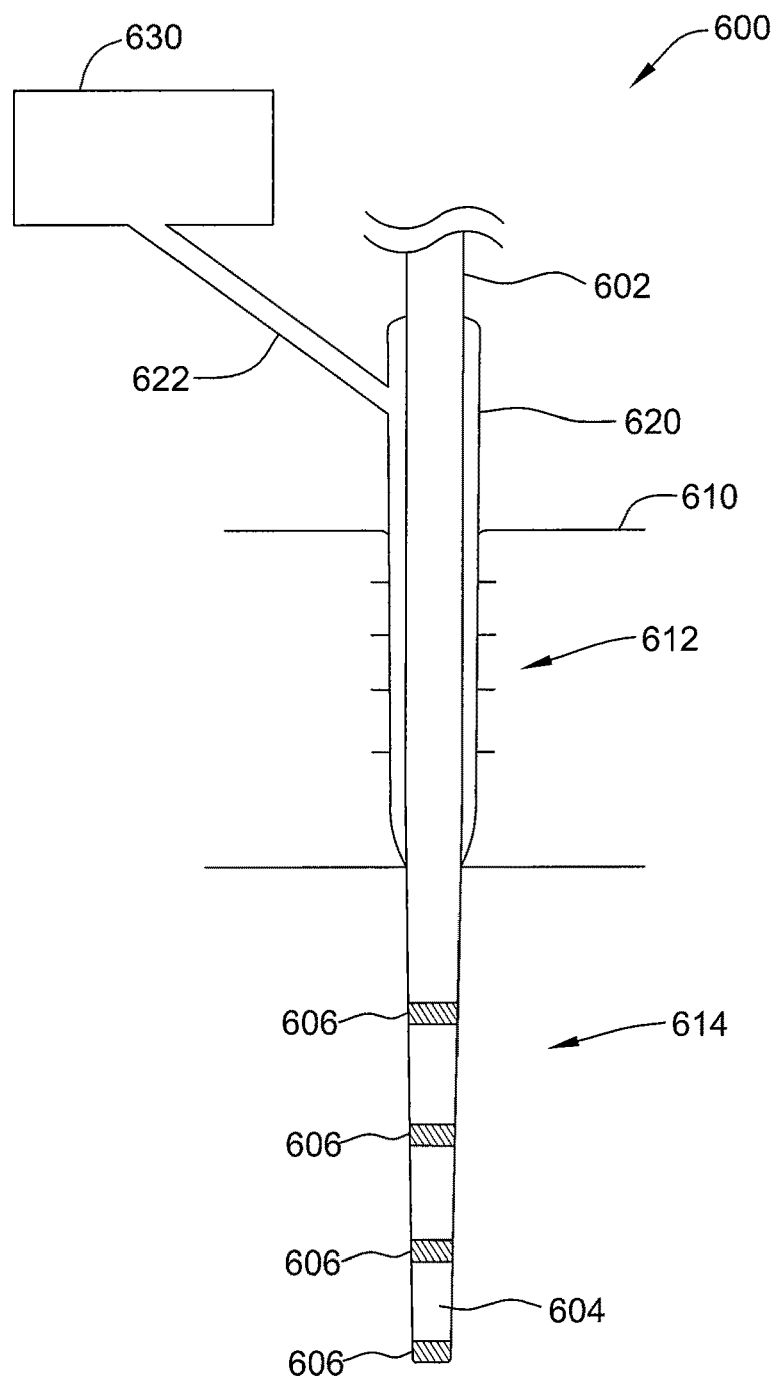
FIG. 6 is a schematic diagram of another embodiment of an SCS lead that may be used to reduce post-operation pain.

FIG. 6 is a schematic diagram of another embodiment of an SCS lead 600 that may be used to reduce post-operation pain. SCS lead 600 includes a lead body 602 that includes a distal end 604. In this embodiment, distal end 604 includes a plurality of distal electrodes 606. After implantation, distal electrodes 606 are configured to apply electrical stimulation to the dorsal column, dorsal root(s), and/or dorsal root ganglia (DRG).

As shown in FIG. 6, SCS lead 600 extends through a patient's skin 610, through subcutaneous tissue 612, and into epidural space 614, such that distal electrodes 606 are located in epidural space 614. An infusion sheath 620 substantially surrounds lead body 602. In this embodiment, infusion sheath 620 surrounds lead body 602 in subcutaneous tissue 612 and at skin 610, but does not surround lead body 602 in epidural space. One or more compounds, such as those described above, may be supplied to infusion sheath 620 through an infusion port 622. This allows the compounds to be injected into subcutaneous tissue 612 to reduce pain. The compounds may include pain relieving drugs, anti-inflammatory medications, anti-biotics, antipyretics, temperature-modulated substances, analgesics, cortocosteriods, and/or neurolytic blocks.

In some embodiments, an external pump 630 is used to supply one or more compounds (e.g., pain relieving drugs) to infusion sheath 620. Alternatively, the compounds may be supplied without using infusion sheath 620. External pump 630 may be suitable pumping device that supplies compounds to infusion sheath 620. For example, external pump 630 may be an osmotic pump (e.g., a pump that uses a molarity difference to drive flow of at least one compound). In another example, external pump 630 uses iontophoresis to drive charged compounds (e.g., pain relieving drugs, carboxylic acid compounds) to electrodes in the incision pocket to facilitate reducing pain. Specifically, an ion-exchange membrane surrounds a source electrode, which contains pain reduction compounds, and an applied electric current is used to drive the compounds into subcutaneous tissue 612.

Figure 7:
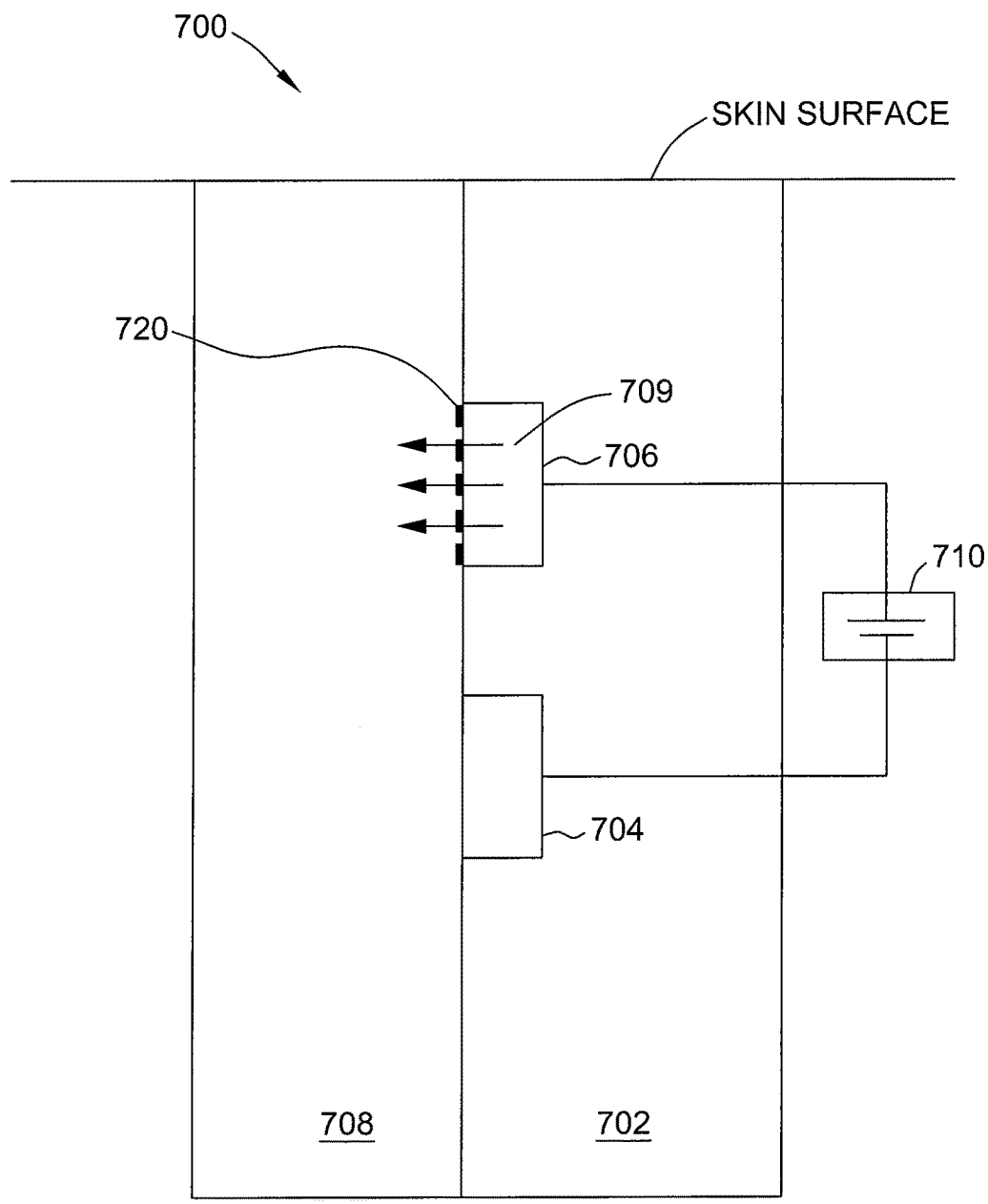
FIG. 7 is a schematic diagram of an SCS lead 700 that uses iontophoresis to deliver at least one compound Corresponding reference characters indicate corresponding parts throughout the several views of the drawings.

For example, FIG. 7 is a schematic diagram of an SCS lead 700 that uses iontophoresis to deliver at least one compound. As shown in FIG. 7, a lead body 702 includes a cathode 704 and an anode 706 adjacent to tissue 708 of a patient. Anode 706 includes a drug reservoir 709 that includes one or more of the compounds described herein. An iontophoresis pump 710 is electrically coupled between cathode 704 and anode 706. Iontophoresis pump 710 may be, for example, a battery or other power source. To deliver the compound in drug reservoir 709 a current is applied using iontophoresis pump 710. The applied current releases the compound into tissue 708 across an ion-exchange membrane 720.

A method for spinal cord stimulation (SCS) is provides using the embodiments described herein. The method includes implanting an SCS lead through an incision site in a patient, the SCS lead including at least one distal electrode configured to apply electrical stimulation to a stimulation target of the patient, and reducing pain at least one of the incision site and a site of an implanted pulse generator after implantation using the SCS lead.

Notably, the systems and methods described herein are not limited to use with a lead for an SCS trial system. That is, the systems and methods described herein may be used for a chronic SCS implantation at the suture site and/or in a pocket where a pulse generator is implanted. Further, features from different embodiments described herein may be combined together. For example, drug delivery mechanisms and PNfS electrodes may be implemented using the same SCS lead.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A spinal cord stimulation (SCS) system comprising:
at least one SCS lead comprising:
a lead body;
at least one distal electrode located at a distal end of the lead body, the at least one distal electrode configured to apply electrical stimulation to a stimulation target of a patient;
a pain reduction assembly coupled to the lead body and configured to reduce post-operation pain at an incision site associated with implantation of the at least one SCS lead, the pain reduction assembly including a slidable sheath that substantially surrounds the lead body, the slidable sheath able to translate relative to the lead body, the slidable sheath including at least one peripheral nerve field stimulation electrode configured to deliver electrical stimulation to tissue proximate to the incision site, the slidable sheath further operative to facilitate adjustable positioning of the at least one peripheral nerve field stimulation electrode in a vicinity of the incision site; and
a pulse generator coupled to the at least one SCS lead and configured to control electrical stimulation delivered to the patient via the at least one SCS lead.

2. The SCS system of claim 1, wherein the slidable sheath including the at least one peripheral nerve field stimulation electrode is secured to surrounding tissue proximate to the incision site using a suture.

3. The SCS system of claim 2, wherein the slidable sheath is positionable along the lead body such that the at least one peripheral nerve field stimulation electrode stimulates dermatomes that correspond to the incision site.

4. The SCS system of claim 1, wherein the pain reduction assembly comprising the at least one peripheral nerve field stimulation electrode is located at a proximal portion of the lead body.

5. The SCS system of claim 1, wherein the slidable sheath includes a sleeve configured to deliver at least one compound to the tissue proximate to the incision site.

6. The SCS system of claim 5, wherein the sleeve comprises a mesh embedded with at least one pain relieving, antibiotic, or anti-inflammatory drug.

7. The SCS system of claim 6, wherein the mesh is a polymer mesh.

8. The SCS system of claim 6, wherein the mesh is a biodegradable mesh.

9. The SCS system of claim 1, wherein the at least one peripheral nerve field stimulation electrode is one of a segmented electrode, a ring electrode and a planar electrode.

10. A spinal cord stimulation (SCS) lead comprising:
a lead body;
at least one distal electrode located at a distal end of the lead body, the at least one distal electrode configured to apply electrical stimulation to a stimulation target of a patient; and
a pain reduction assembly coupled to the lead body and configured to reduce post-operation pain at an incision site associated with implantation of the SCS lead, the pain reduction assembly including a slidable sheath that substantially surrounds the lead body, the slidable sheath able to translate relative to the lead body, the slidable sheath including at least one peripheral nerve field stimulation electrode configured to deliver electrical stimulation to tissue proximate to the incision site, the slidable sheath further operative to facilitate adjustable positioning of the at least one peripheral nerve field stimulation electrode in a vicinity of the incision site.

11. The SCS lead of claim 10, wherein the pain reduction assembly comprising the at least one peripheral nerve field stimulation electrode is located at a proximal portion of the lead body.

12. The SCS lead of claim 11, wherein the slidable sheath comprises a sleeve configured to deliver at least one compound to the tissue proximate to the incision site.

13. The SCS lead of claim 12, wherein the sleeve comprises a mesh formed of one of a polymer material and a biodegradable material embedded with the at least one compound comprising at least one of a pain relieving drug, an antibiotic drug and an anti-inflammatory drug.

14. The SCS lead of claim 9, wherein the at least one peripheral nerve field stimulation electrode is one of a segmented electrode, a ring electrode and a planar electrode.

* * * * *